(12) United States Patent
Maeda

(10) Patent No.: US 9,976,997 B2
(45) Date of Patent: May 22, 2018

(54) DATA PROCESSING DEVICE FOR QUANTITATION

(71) Applicant: SHIMADZU CORPORATION, Kyoto-shi, Kyoto (JP)

(72) Inventor: Kazuma Maeda, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 46 days.

(21) Appl. No.: 15/294,928

(22) Filed: Oct. 17, 2016

(65) Prior Publication Data

US 2018/0106771 A1   Apr. 19, 2018

(51) Int. Cl.
*G01N 31/00*    (2006.01)
*G01N 30/86*    (2006.01)
*G01N 30/72*    (2006.01)

(52) U.S. Cl.
CPC ......... *G01N 30/8631* (2013.01); *G01N 30/72* (2013.01)

(58) Field of Classification Search
CPC ........... G01N 15/06; G01N 2015/0038; G01N 21/359
USPC ..................................... 702/22, 23
See application file for complete search history.

(56) References Cited

U.S. PATENT DOCUMENTS

| 9,572,497 B2* | 2/2017 | Razansky ............ A61B 5/0073 |
| 9,659,759 B2* | 5/2017 | Panchagnula ...... G01N 33/6803 |
| 2014/0278143 A1* | 9/2014 | Garstecki ............... G01N 15/06 702/23 |

FOREIGN PATENT DOCUMENTS

| JP | 60-073436 A | 4/1985 |
| JP | 02-245664 A | 10/1990 |

* cited by examiner

*Primary Examiner* — An Do
(74) *Attorney, Agent, or Firm* — Sughrue Mion, PLLC

(57) ABSTRACT

When there are a plurality of concentration value candidates, an extreme value of the calibration curve is detected, and the number of calibration points respectively contained in a region having a low concentration and a region having a high concentration is calculated using the extreme value as a boundary. If there is a difference between the numbers of calibration points of both regions, a concentration value candidate present in the region having a larger number of calibration points is selected as a quantitation result. When the numbers of calibration points are the same, the sign of the coefficient of the term of the second degree of the calibration curve is assessed, and a concentration value candidate present in a region in which the relationship between peak area values and concentration values is monotonically increasing is selected as a quantitation result.

14 Claims, 9 Drawing Sheets

DATA PROCESSING DEVICE FOR QUANTITATION

This application incorporates by reference in its entirety the disclosure in Japanese Patent publication 2015-224889, published Dec. 14, 2015, to the same inventors.

TECHNICAL FIELD

The present invention relates to a data processing device for quantitation for quantifying an amount of a component or a component concentration in a sample using a calibration curve created in advance in various analysis devices or measurement devices including a chromatography device such as a liquid chromatograph (LC) or a gas chromatograph (GC) or a mass spectrometer.

BACKGROUND ART

When investigating the concentration or amount of a specific compound contained in a sample using a chromatography device or a mass spectrometer, a calibration curve created on the basis of the results of analyzing a reference sample or the like with a known concentration is typically used. More specifically, in a chromatography device, a chromatogram for each concentration is created by measuring each reference sample containing a specific compound having a plurality of stages of known concentrations, and the area of a peak or the height of the top of a peak corresponding to the compound is determined in each chromatogram. An approximate mathematical formula expressing a curve (or a line) for which the error with respect to a plurality of calibration points indicating the relationship between the concentration of the compound and the peak area value or the peak height value is smallest is then found as a calibration curve. This mathematical formula expressing a calibration curve is stored in a storage part, and when a measurement value for a compound with an unknown concentration (that is, the peak area value or the peak height value in a chromatogram) is provided, the measurement value is compared with the calibration curve to calculate a quantitative value (concentration value). In recent analysis devices, the creation of a calibration curve on the basis of a plurality of calibration points as described above is performed automatically by a data processing device realized by executing dedicated software for data processing installed on a personal computer (see Patent Documents 1, 2, and the like).

In a quantitative analysis device using a calibration curve, the precision of the calibration curve influences the precision of a quantitative value. Therefore, in a conventional data processing device for quantitation, for example, an operator can select either a quadratic function or a cubic function as a mathematical function for automatically creating a calibration curve, and the coefficients of the terms of each degree in the selected function are calculated on the basis of a plurality of provided calibration points. FIG. 4 illustrates an example of a calibration curve determined by a quadratic function, and FIG. 5 illustrates an example of a calibration curve determined by a cubic function. When either a quadric function or a cubic function is selected by the operator as a function for expressing a mathematical formula of a calibration curve, the most probable curve (ordinarily a curve with the smallest error with respect to a plurality of calibration points) is calculated on the premise of the function of the selected degree, and the mathematical formula expressing this curve serves as a calibration curve.

When the calibration curve is a second degree or higher function rather than a straight line, the solution—that is, the concentration value—with respect to a measurement value (for example, a peak area value) is sometimes not determined uniquely. For example, when a calibration curve such as that illustrated in FIG. 4 is obtained and the peak area value is a value indicated by P1 in FIG. 4, there are two candidates Q1 and Q2 for the concentration value, and it is uncertain which is the value. In addition, when a calibration curve such as that illustrated in FIG. 5 is obtained and the peak area value is a value indicated by P1 in FIG. 5, there are three candidates Q1, Q2, and Q3 for the concentration value, and it is uncertain which is the value. Therefore, when there are a plurality of candidates for the concentration value based on the calibration curve in this way, one method of selecting a valid candidate is a method of selecting a candidate which falls within a concentration measurement range defined by calibration points.

In the example of FIG. 4, the maximum value of the concentration indicated by the calibration points is Dmax, and the minimum value is Dmin, so the concentration measurement range is Dmin to Dmax. While the concentration value candidate Q2 falls within this concentration measurement range, the concentration value candidate Q1 does not fall within this concentration measurement range. Therefore, it is assessed that the concentration value candidate Q2 is valid, and Q2 is outputted as a concentration value serving as a quantitation result.

However, a quantitative value selected by a method such as that described above from among a plurality of candidates cannot necessarily be considered appropriate. The reason for this is as follows.

That is, in calibration curve automatic creation processing such as that described above, a calibration curve of a quadratic function or a cubic function that is valid for all of a plurality of provided calibration points. Therefore, when four calibration points are provided, as illustrated in FIG. 4, for example, even if one of the calibration points with a concentration value of Q2 or higher is erroneous (or inappropriate), a calibration curve with a shape such as that illustrated by the solid line in FIG. 4 is created. If this erroneous calibration point had not been provided, a calibration curve with a shape such as that illustrated by the dotted and dashed line in FIG. 4 should have been created. Assuming that this is the case, the concentration value selected by the method described above from a plurality of candidates diverges substantially from the actual concentration value, and it can be considered extremely inappropriate to output this value as a quantitation result.

In addition, depending on the type of analysis or measurement, there are also cases in which the relationship between quantitative values (concentration values) and measurement values (peak area values) is actually as illustrated by the solid line in FIG. 4 or 5. In such cases, the calibration curve with the shape illustrated in FIG. 4 or 5 is not itself erroneous. However, when quantitation is performed using a calibration curve, it is rarely the case that it is desirable to perform quantitation within both a measurement value increasing range and a measurement value decreasing range associated with increases in concentration, and it is typical to perform quantitation in only one range or the other. In such cases as well, it is not possible to select an appropriate quantitative value from a plurality of candidates with the method described above. For example, in the example of FIG. 4, although it is more appropriate to output the concentration value Q1 present in a measurement value increasing range associated with an increase in concentration as a quantitation result, the concentration value Q2, which differs from the intention of the person making the measurement, is outputted as a quantitation value.

PRIOR ART DOCUMENTS

Patent Documents

[Patent document 1] Japanese Unexamined Patent Application Publication No. S60-73436
[Patent document 2] Japanese Unexamined Patent Application Publication No. H2-245664

SUMMARY OF THE INVENTION

Problem to be Solved by the Invention

The present invention was conceived in light of the problem described above, and an object thereof is to provide a data processing device for quantitation which is capable of deriving a quantitative value of higher validity when a calibration curve has a curved shape approximated by a quadratic function, a cubic function, or the like and there are a plurality of solutions—that is, quantitative values—for a measurement value.

Means for Solving the Problem

A first invention conceived in order to solve the problem described above is a data processing device for quantitation for deriving a quantitative value corresponding to a target measurement value using a calibration curve indicating a relationship between measurement values and quantitative values determined by a polynomial function, the calibration curve being created on the basis of a plurality of calibration points; the data processing device for quantitation comprising:

a) an extreme value acquisition part for retrieving an extreme value in the calibration curve;

b) a quantitative value region extraction part for extracting a region where a number of calibration points is maximized by partitioning an entire range of quantitative values determined using a quantitative value corresponding to the obtained extreme value as a boundary into a plurality of regions and determining a number of calibration points contained in each region; and c) a quantitative value determination part for referencing the calibration curve and, if there are a plurality of quantitative values corresponding to the target measurement value, selecting a quantitative value contained in the region extracted by the quantitative value region extraction part as a valid quantitation result.

When the data processing device for quantitation according to the first invention and the second invention described below is used for quantitative analysis with a chromatography device (including a chromatographic mass spectrometer having a mass spectrometer as a detector), the measurement value described above is the area value or height value of a peak in the chromatogram.

In the data processing device for quantitation according to the first invention and the second invention described below, the degree of the polynomial function is not particularly limited to two or greater, but the polynomial function is a quadratic function or a cubic function from a practical standpoint. When a quadratic function is used as a calibration curve, there is only one extreme value (maximum value or minimum value) retrieved by the extreme value acquisition part, so there are two of the regions described above. On the other hand, when a cubic function is used as a calibration curve, there are two extreme values (maximum value and minimum value) retrieved by the extreme value acquisition part, so there are three of the regions described above.

One region of quantitative values is a range in which the quantitative values monotonically increase or monotonically decrease as the measurement values increase. In order to create a calibration curve with high precision when creating a calibration curve for quantitation, the spacing of calibration points is typically made narrow (the step width of quantitative values is made small) in the quantitative value range over which quantitation is to be performed, and the spacing of calibration points is widened or calibration points are omitted in quantitative value ranges which are not important for quantitation. Therefore, a region having a large number of calibration points among a plurality of regions determined using a quantitative value corresponding to an extreme value of the calibration curve as a boundary is highly likely to be the quantitative value range on which the person making the measurement is focusing attention (that is, the range over which quantitative analysis is to be performed). Therefore, in the data processing device for quantitation according to the first invention, the quantitative value region extraction part determines the number of included calibration points for each region and extracts the region with the maximum number of calibration points. The calibration curve is then referenced, and if there are a plurality of quantitative values corresponding to the target measurement value, the quantitative value determination part selects a value contained in the extracted region as a valid quantitation result.

In this data processing device for quantitation of the first invention, the matter of whether the quantitative value determined by comparing the target measurement value to the calibration curve is present within a measurement concentration range determined by the calibration point yielding the maximum quantitative value and the calibration point yielding the minimum quantitative value is unrelated to the selection of the quantitative value. Therefore, even if a candidate for a quantitative value corresponding to the target measurement value does not fall within the measurement concentration range, it is possible to automatically select a quantitative value candidate of highly validity in the calibration curve—that is, a quantitative value candidate present in a monotonically increasing range or a monotonically decreasing range that the person in charge of creating the calibration curve can be presumed to have been considering. As a result, a quantitative value with a high probability can be determined as a quantitation result.

In addition, in the data processing device for quantitation according to the first invention, when a quantitative value assessed to be valid is a negative value, the quantitative value determination part uses the negative value directly as a quantitation result or replaces the quantitation result with zero and then implements a display making it possible to identify that the quantitation result was replaced.

In actuality, it is impossible for a quantitative value to assume a negative value, but depending on the calibration curve that is created, a quantitative value corresponding to a target measurement value may assume a negative value mathematically. In this case, it is obvious that the obtained quantitation result is not appropriate, but with the configuration described above, the person making the measurement can understand at a glance that the result is not appropriate, which makes it possible to reduce operational mistakes related to quantitative analysis.

In addition, when the numbers of calibration points in a plurality of regions determined using quantitative values corresponding to extreme values as boundaries are the same in at least two regions, it is necessary to select one of the regions. The selection method may be determined appropriately in accordance with the type of the analysis device/measurement device or the like.

For example, in many quantitative analyses, quantitation is performed in a state in which measurement values increase as quantitative values of concentration or the like increase, so a region over which the relationship between the measurement values and the quantitative values is monotonically increasing should be selected. When the calibration curve is a quadratic function, it can be discriminated whether a region that is monotonically increasing is smaller or larger than an extreme value by assessing the sign of the coefficient of the term of the second degree.

In addition, a second invention conceived in order to solve the problem described above is a data processing device for quantitation for deriving a quantitative value corresponding to a target measurement value using a calibration curve indicating a relationship between a measurement value and a quantitative value determined by a polynomial function, the calibration curve being created on the basis of a plurality of calibration points; the data processing device for quantitation comprising:

a) a lower detection point extraction point for, when there are detection points for which measurement values are smaller than the target measurement value, extracting a detection point for which a measurement value is closest to the target measurement value as a lower detection point from among the detection points;

b) an upper detection point extraction point for, when there are detection points for which measurement values are smaller than the target measurement value, extracting a detection point for which a measurement value is closest to the target measurement value as an upper detection point from among the detection points; and c) a quantitative value determination part for referencing the calibration curve and, if there are a plurality of quantitative values corresponding to the target measurement value and both a lower detection point and an upper detection point are present, assessing that a quantitative value candidate contained in a quantitative value range between a quantitative value corresponding to the lower detection point and a quantitative value corresponding to the upper detection point is a valid solution.

When there is one quantitative value candidate contained in the quantitative value range, the quantitative value determination part should use the candidate as the quantitation result, but when there are a plurality of quantitative value candidates contained in the quantitative value range, it is necessary to select one of the candidates. Therefore, in the data processing device for quantitation according to the second invention, when there are a plurality of quantitative value candidates contained in the quantitative value range, a detection point for which a measurement point is closer to the target measurement value is preferably found from among the lower detection point and the upper detection point and used as a proximate detection point, and it should be assessed that a quantitative value candidate contained in a region where the proximate detection point is present is the only valid solution among the plurality of regions into which the quantitative values are partitioned using quantitative values corresponding to extreme values of the calibration curve as boundaries.

In addition, in the data processing device for quantitation according to the second invention, the quantitative value determination part should be configured to reference the calibration curve and, if there are a plurality of quantitative values corresponding to the target measurement value and only either a lower detection point or an upper detection point is present, to assess that a quantitative value candidate contained in a region where the present lower detection point or upper detection point is present is a valid solution.

With this data processing device for quantitation according to the second invention as well, there is a high likelihood of being able to select a quantitative value candidate present in the vicinity of a range in which calibration points are relatively closely packed in the quantitative value direction. As described above, since the likelihood that a range in which calibration points are relatively closely packed is the quantitative value range on which the person making the measurement is focusing attention, it can be considered highly likely that the selected quantitative value candidate is the desired quantitative result of the person making the measurement, and a valid quantitative result can be provided to the person making the measurement.

Effect of the Invention

With the data processing devices for quantitation according to the first and second inventions, even if the calibration curve has a curved shape approximated by a quadratic function, a cubic function, or the like and there are a plurality of solutions—that is, quantitative values—for a measurement value, a quantitative value of higher validity can be derived. As a result, it is less likely for an inappropriate quantitative value that does not conform to the intention of the person making the measurement to be outputted as a quantitation result, which makes it possible to perform quantitative analysis of higher accuracy than conventional devices.

In addition, with the data processing devices for quantitation according to the first and second inventions, it is possible to select a quantitative value corresponding to a target measurement value irrespective of a quantitative value range determined by a calibration point corresponding to the minimum quantitative value and a calibration point corresponding to the maximum value—that is, regardless of whether the quantitative value is within this quantitative value range or deviates from the range. Therefore, when selecting calibration points to create a calibration curve, for example, restrictions related to the selection of calibration points, such as necessarily selecting at least one calibration point with a higher concentration and one calibration point with a lower concentration than the concentration of a sample component to be measured, are eliminated. As a result, the degrees of freedom of the method of selecting calibration points increase, and the burden on the person making the measurement is reduced.

DETAILED DESCRIPTION OF THE EXEMPLARY EMBODIMENTS

Figure 1:
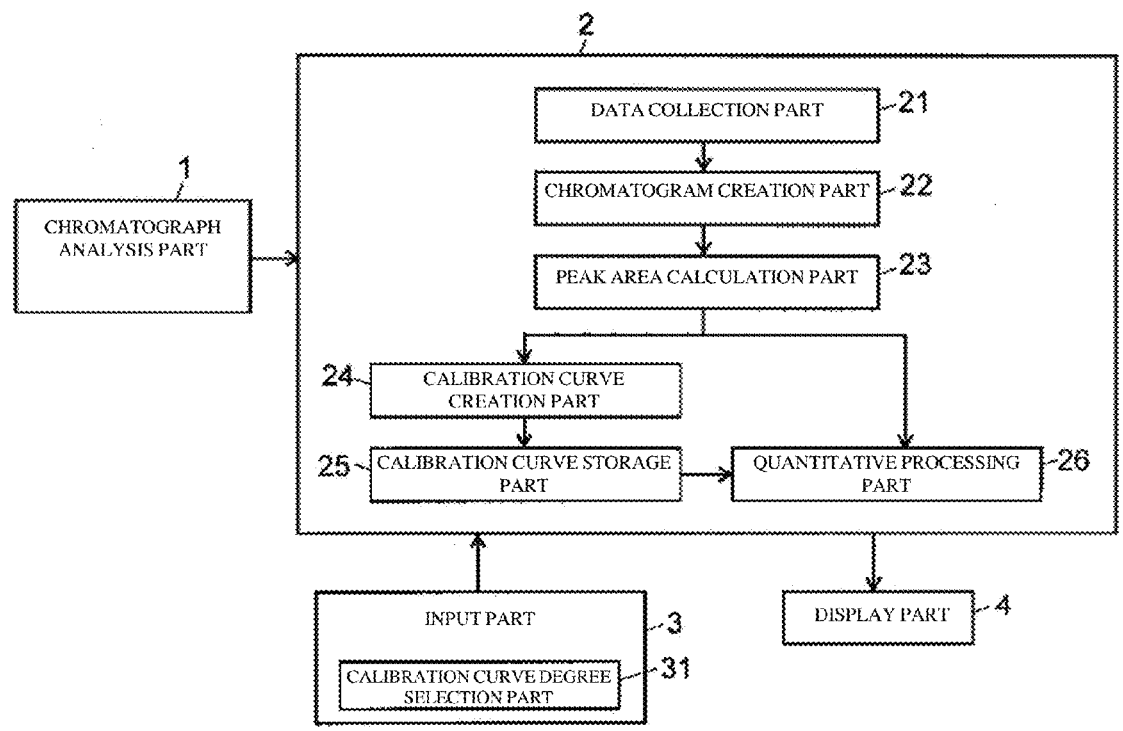
FIG. 1 is a schematic block diagram of an embodiment (first embodiment) of a chromatography device provided with the data processing device for quantitation according to the present invention.

An embodiment of the data processing device for quantitation according to the present invention will be described hereinafter with reference to the attached drawings. FIG. 1 is a schematic block diagram of a chromatography device provided with the data processing device for quantitation according to a first embodiment.

This chromatography device comprises a chromatograph analysis part 1 for performing chromatographic analysis on a sample and a data processing part 2 for performing quantitative analysis using data obtained in chromatographic analysis. The chromatograph analysis part 1 may be any of a GC, LC, GC-MS, LC-MS, or the like. The data processing part 2 comprises a data collection part 21, a chromatogram creation part 22, a peak area calculation part 23, a calibration curve creation processing part 24, a calibration curve storage part 25, and a quantitative processing part 26 as functional blocks. In addition, an input part 3 comprising a calibration curve degree selection part 31 and a display part 4 for displaying a quantitation result or the like are connected to the data processing part 2. The substance of this data processing part 2 is a personal computer on which dedicated data processing software is installed, and the functions of each of the parts described above are realized by the execution of this software on the computer.

When performing quantitative analysis in this chromatography device, a measurement is performed on a reference sample containing a specific compound with a known concentration at an appropriate point in time prior to quantitative analysis, and a calibration curve is created on the basis of this result.

That is, reference samples having a plurality of stages (n stages in this example) of concentrations are respectively measured with the chromatograph analysis part 1, the data collection part 21 collects chromatogram data obtained by this measurement. The chromatogram creation part 22 creates a chromatogram for each different concentration on the basis of the collected chromatogram data. The peak area calculation part 23 detects a peak corresponding to the specific compound in the chromatogram on the basis of the known retention time of the specific compound and calculates the area value of the peak. As a result, n calibration points indicating the relationship between the concentration values and the peak area values of the specific compound are determined.

The calibration curve creation processing part 24 creates a calibration curve based on a maximum of n calibration points that are provided in response to an instruction from the input part 3 by an analyzer. The calibration points used to create the calibration curve can be selected appropriately by the analyzer. That is, all n of the calibration points may be used to create the calibration curve, or the calibration points considered to be obviously abnormal values when observed by the analyzer may be removed. In addition, at the time of the creation of the calibration curve, the analyzer designates whether to use either a quadratic function or a cubic function as a calibration curve with the calibration curve degree selection part 31.

Using the designated quadratic function or cubic function as a premise, the calibration curve creation processing part 24 creates a curve that most precisely fits the plurality (ordinarily three or more) of provided calibration points and determines a mathematical formula expressing this curve.

Figure 4:
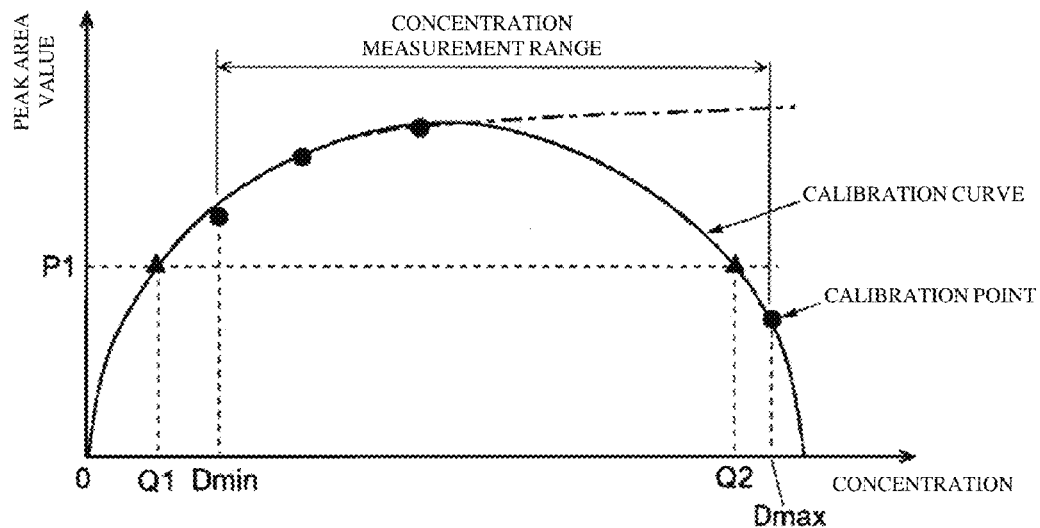
FIG. 4 illustrates an example of a calibration curve when the calibration curve is a quadratic function.
Figure 5:
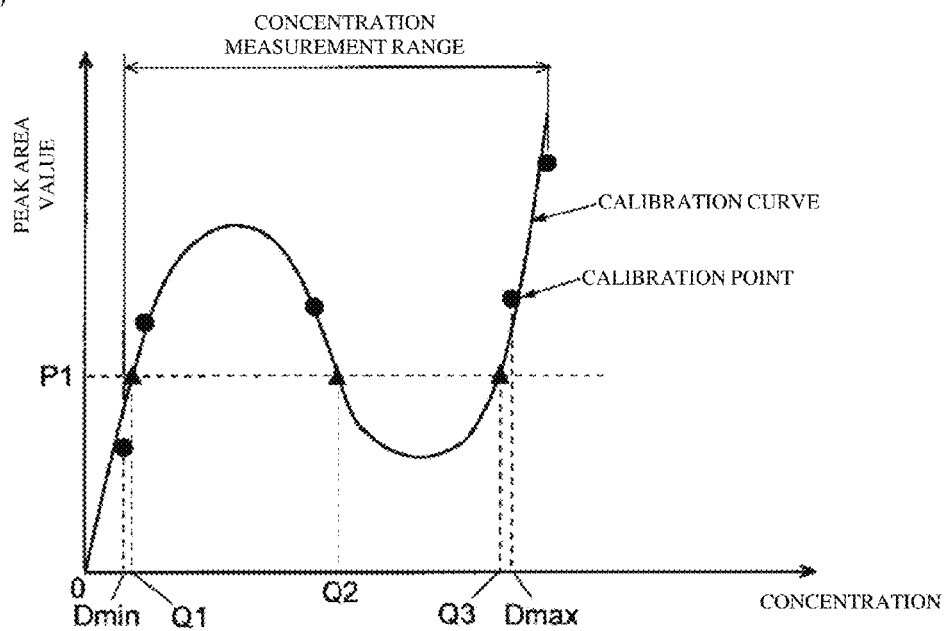
FIG. 5 illustrates an example of a calibration curve when the calibration curve is a cubic function.

As a result, for example, a calibration curve such as that illustrated in FIG. 4 is created when the function is a quadratic function, and a calibration curve such as that illustrated in FIG. 5 is created when the function is a cubic function. The mathematical formula expressing such a calibration curve is stored in the calibration curve storage part 25. In addition, the calibration points used to create the calibration curve are also stored in the calibration curve storage part 25.

When performing quantitative analysis on an unknown sample containing a specific compound with an unknown concentration, the unknown sample is measured with the chromatograph analysis part 1, and the data collection part 21 collects the chromatogram data obtained by this measurement. The chromatogram creation part 22 creates a chromatogram on the basis of the collected chromatogram data. The peak area calculation part 23 detects a peak corresponding to the specific compound in the chromatogram on the basis of the known retention time of the specific compound and calculates the area value of the peak.

The quantitative processing part 26 reads out the calibration curve from the calibration curve storage part 25 and determines a concentration value by comparing the peak area value to the calibration curve. When a single concentration value is determined for the peak area value, the concentration value is outputted to the display part 4 as a quantitation result, and the display part 4 displays the quantitation result on a screen. However, depending on the curved shape of the calibration curve or the value of the peak area, there are cases in which a plurality of concentration values are determined as quantitation result candidates for the peak area value. In such cases, the quantitative processing part 26 performs the processing illustrated in FIG. 2 or 3 depending on whether the calibration curve is a quadratic function or a cubic function.

Figure 2:
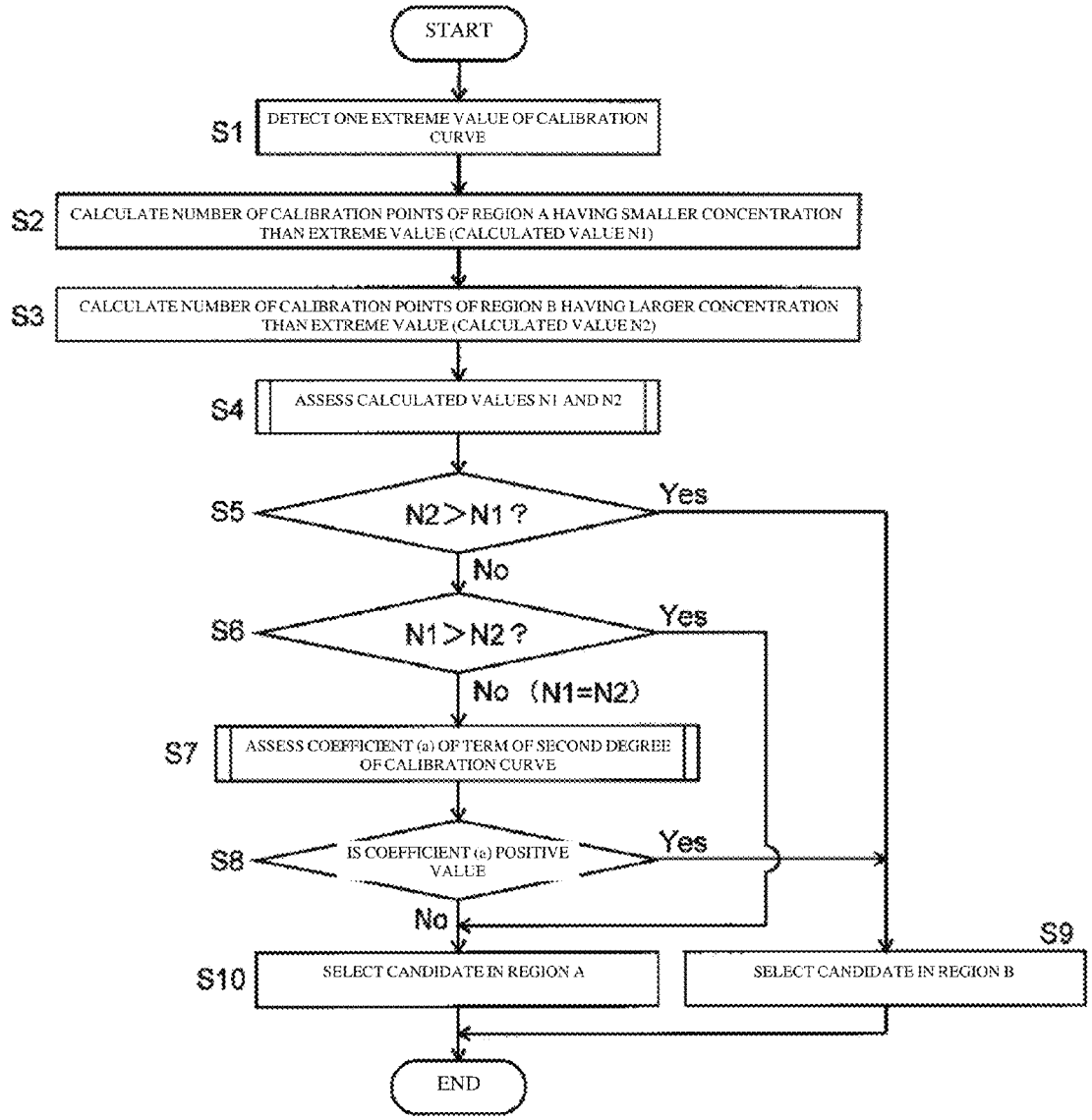
FIG. 2 is a flowchart of the processing for selecting a concentration value candidate when the calibration curve is a quadratic function in the data processing for quantitation according to the first embodiment.

The data processing for selecting a concentration value candidate when the calibration curve is a quadratic function will be described using the flowchart illustrated in FIG. 2.

When processing is initiated, the quantitative processing part 26 detects one extreme value (maximum value or minimum value) of the calibration curve, which is a quadratic function (step S1). Next, the number of calibration points contained in a region A in which the concentration values are smaller than the extreme value is calculated for a plurality of calibration points used to create the calibration curve, and the calculated value is defined as N1 (step S2). Simultaneously, the number of calibration points contained in a region B in which the concentration values are larger than the extreme value is calculated, and the calculated value is defined as N2 (step S3). The calculated value N1 and the calculated value N2 are then assessed (step S4). That is, it is assessed whether the calculated value N2 is larger than the calculated value N1 (step S5), and if an assessment of "Yes" is made in step S5, a candidate contained in region B in which the concentration values are larger than the extreme value is selected as a quantitation result (step S9). On the other hand, if an assessment of "No" is made in step S5, it is assessed whether the calculated value N1 is greater than the calculated value N2 (step S6). If an assessment of "Yes" is made in step S6, a candidate contained in region A in which the concentration is smaller than the extreme value is selected as a quantitation result (step S10).

Figure 6:
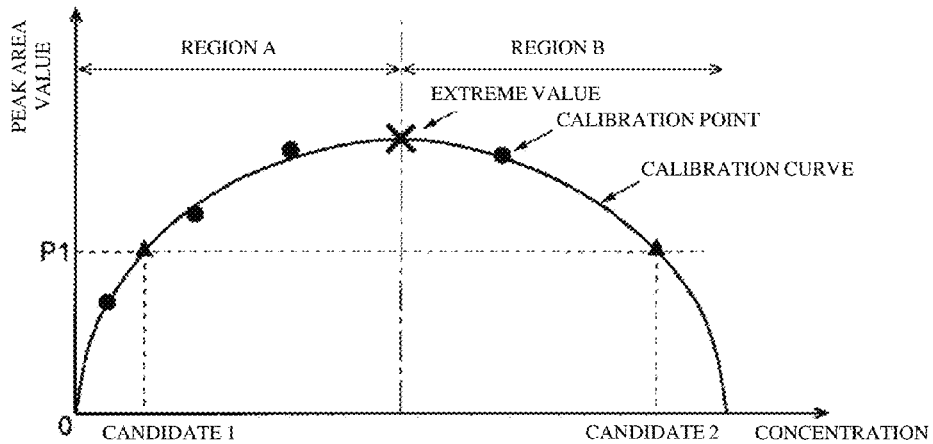
FIG. 6 is an explanatory diagram of the selection operation for a concentration value candidate when the calibration curve is a quadratic function.
Figure 8:
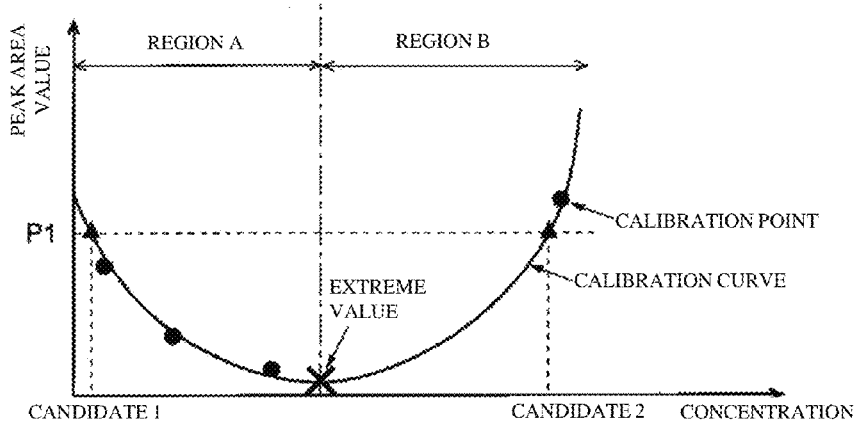
FIG. 8 is an explanatory diagram of the selection operation for a concentration value candidate when the calibration curve is a quadratic function.

FIGS. 6 and 8 are explanatory diagrams of examples of the selection operation for a concentration value candidate when an assessment of "Yes" is made in either of steps S5 or S6. In the example of FIG. 6, N1=3 and N2=1, and since N1>N2, a concentration value candidate 1 in region A is selected as a quantitation result for a peak area value P1 as a result of the processing of step S10. On the other hand, FIG. 8 is an example of case in which the calibration curve has a downward convex shape in the opposite manner as in FIG. 5, but in this case as well, N1=3 and N2=1, and since N1>N2, a concentration value candidate 1 in region A is selected as a quantitation result for the peak area value P1 as a result of the processing of step S10. As can be seen from FIG. 8, this concentration value candidate 1 indicates a concentration value that is even smaller than the smallest calibration point, but this does not affect the selection of the candidate.

If an assessment of "No" is made in both steps S5 and S6 described above, the calculated value N1 and the calculated value N2 are the same values. In this case, it is assessed whether the coefficient (a) of the term of the second degree of the calibration curve is a positive value (steps S7 and S8). When the shape of the calibration curve is a downward convex curved shape (that is, the extreme value is the minimum value) such as those illustrated in FIGS. 7 and 8, the coefficient (a) is a positive value. In addition, when the shape of the calibration curve is an upward convex curved shape (that is, the extreme value is the maximum value) such as that illustrated in FIG. 6, the coefficient (a) is a negative value.

That is, when the coefficient (a) is a positive value, the peak area value monotonically increases with respect to increases in concentration in region B in which the concentration is larger than the extreme value. On the other hand, when the coefficient (a) is a negative value, the peak area value monotonously increases with respect to increases in concentration in region A in which the concentration is lower than the extreme value.

In chromatographic analysis, quantitation is typically performed in a state in which the peak area values increase as the concentration values increase—that is, when the relationship between the concentration values and the peak area values is monotonically increasing.

Therefore, if an assessment of "Yes" is made in step S8, the routine proceeds to step S9 described above, wherein a candidate for a concentration value in region B in which the concentration values are larger than the extreme value—that is, a candidate for a concentration value present in a range in which the calibration curve is monotonically increasing—is selected as a quantitation result. Conversely, if an assessment of "No" is made in step S8, the routine proceeds to step S10 described above, wherein a candidate for a concentration value in region A in which the concentration values are smaller than the extreme value—that is, a candidate for a concentration value present in a range in which the calibration curve is monotonically increasing—is selected as a quantitation result. As a result, it is possible to reliably select a candidate for a concentration value in a range in which the calibration curve is monotonically increasing.

Figure 7:
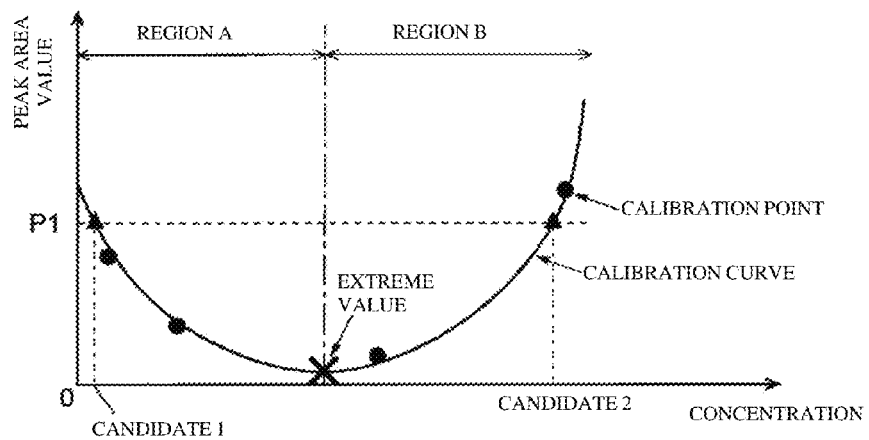
FIG. 7 is an explanatory diagram of the selection operation for a concentration value candidate when the calibration curve is a quadratic function.

FIG. 7 is an explanatory diagram of an example of the selection operation for a concentration value candidate when an assessment of "No" is made in step S6. In this case, N1=N2=2, and since the coefficient (a) is a positive number, a concentration value candidate 2 in region B is selected as a quantitation result for the peak area value P1 as a result of the processing of step S9.

Figure 3:
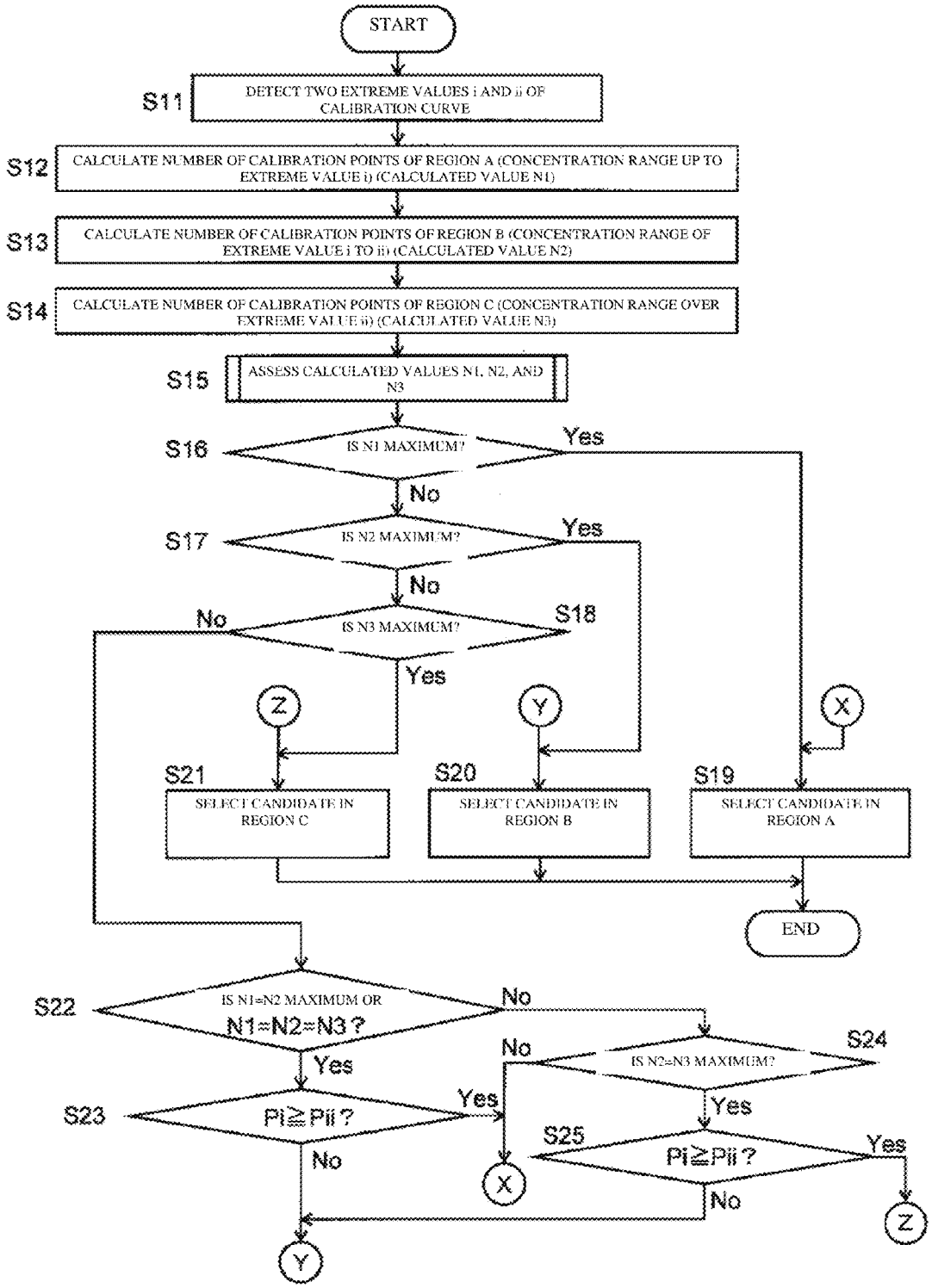
FIG. 3 is a flowchart of the processing for selecting a concentration value candidate when the calibration curve is a cubic function in the data processing for quantitation according to the first embodiment.

Next, the data processing for selecting a concentration value candidate when the calibration curve is a cubic function will be described using the flowchart illustrated in FIG. 3.

In this case, there are two extreme values present, so for the sake of convenience, the extreme value with the lower concentration will be defined as the extreme value i, and the extreme value with the higher concentration will be defined as the extreme value ii here.

When processing is initiated, the quantitative processing part 26 detects the two extreme values i and ii (maximum values or minimum values) of the calibration curve, which is a cubic function (step S11). Next, the number of calibration points contained in each of a region A in which the concentration values are less than the concentration value of the extreme value i, a region B in which the concentration values are greater than or equal to the concentration value of the extreme value i and less than the concentration value of the extreme value ii, and a region C in which the concentration values are greater than or equal to the extreme value ii is respectively calculated for a plurality of calibration points used to create the calibration curve, and the respective calculated values are defined as N1, N2, and N3 (steps S12 to S14). The calculated values N1, N2, and N3 are then assessed (step S15).

That is, it is first assessed whether N1 is the largest among the calculated values N1 to N3 (step S16), and if an assessment of "Yes" is made in step S16, a concentration value candidate present in region A is selected as a quantitation result (step S19). If an assessment of "No" is made in step S16, it is assessed whether N2 is the largest among the calculated values N1 to N3 (step S17), and if an assessment of "Yes" is made in step S17, a concentration value candidate present in region B is selected as a quantitation result (step S20). If an assessment of "No" is made in step S17, it is assessed whether N3 is the largest among the calculated values N1 to N3 (step S18), and if an assessment of "Yes"

is made in step S18, a concentration value candidate present in region C is selected as a quantitation result (step S21).

Figure 10:
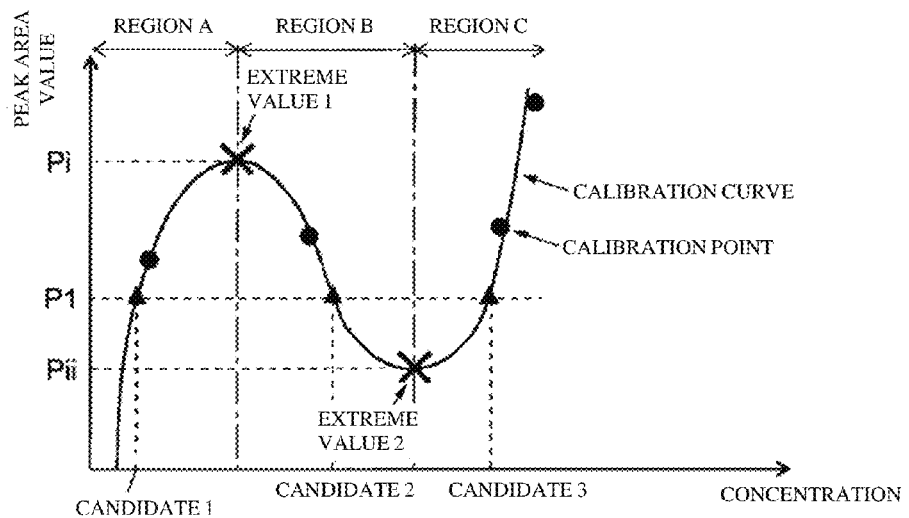
FIG. 10 is an explanatory diagram of the selection operation for a concentration value candidate when the calibration curve is a cubic function.

As a result of the processing of steps S16 to S21 described above, a candidate for a concentration value present in a region having the greatest number of calibration points among the three regions A, B, and C partitioned using the extreme values i and ii as boundaries is selected as a quantitation result. FIG. 10 is an explanatory diagram of an example of the selection operation for a concentration value candidate when an assessment of "Yes" is made in step S18. In the example of FIG. 10, N1=1, N2=1, and N3=2, and since N3>N1 and N2, a concentration value candidate 3 in a region C is selected as a quantitation result for the peak area value P1 as a result of the processing of step S21.

If an assessment of "No" is made in step S18, at least two of the three calculated values N1 to N3 are the same values. Therefore, it is assessed whether the calculated values N1 and N2 are the same and are greater than N3 or whether all three calculated values N1 to N3 are the same (step S22). If an assessment of "Yes" is made in step S22, it is then assessed whether the peak area value Pi of the extreme value i is greater than or equal to the peak area value Pii of the extreme value ii (step S23). An assessment of "Yes" in step S23 means that the relationship between the concentration values and the peak area values is monotonically increasing in the regions A and C and monotonically decreasing in region B. Therefore, in this case, the routine proceeds to step S19, wherein a larger calculated value is obtained and a concentration value candidate present in region A, which is a monotonically increasing range, is selected as a quantitation result. On the other hand, if an assessment of "No" is made in step S23, region B is a monotonically increasing range, so the routine proceeds to step S20, wherein a concentration value candidate present in region B is selected.

In addition, if an assessment of "No" is made in step S22, it is assessed whether the calculated values N2 and N3 are the same and are greater than N1 (step S24). If an assessment of "Yes" is made in step S24, as in step S23, it is then assessed whether the peak area value Pi of the extreme value i is greater than or equal to the peak area value Pii of the extreme value ii (step S25). If an assessment of "Yes" is made in step S25, the routine proceeds to step S21, wherein a larger calculated value is provided and a concentration value candidate in region C, which is a monotonically increasing region, is selected as a quantitation result. On the other hand, an assessment of "No" is made in step S25, region B is a monotonically increasing range, so the routine proceeds to step S20, wherein a concentration value candidate present in region B is selected.

If an assessment of "No" is made in step S24, the calculated values N1 and N3 are the same and are greater than N2. Therefore, the value with the smaller concentration value is given priority, and the routine proceeds to step S19, wherein a concentration value candidate present in region A is selected as a quantitation result.

As a result of the processing of steps S19 to S25, it is possible to reliably select a candidate for a concentration value present in a range in which the concentration values and the peak area values have a monotonically increasing relationship, as described above.

Figure 11:
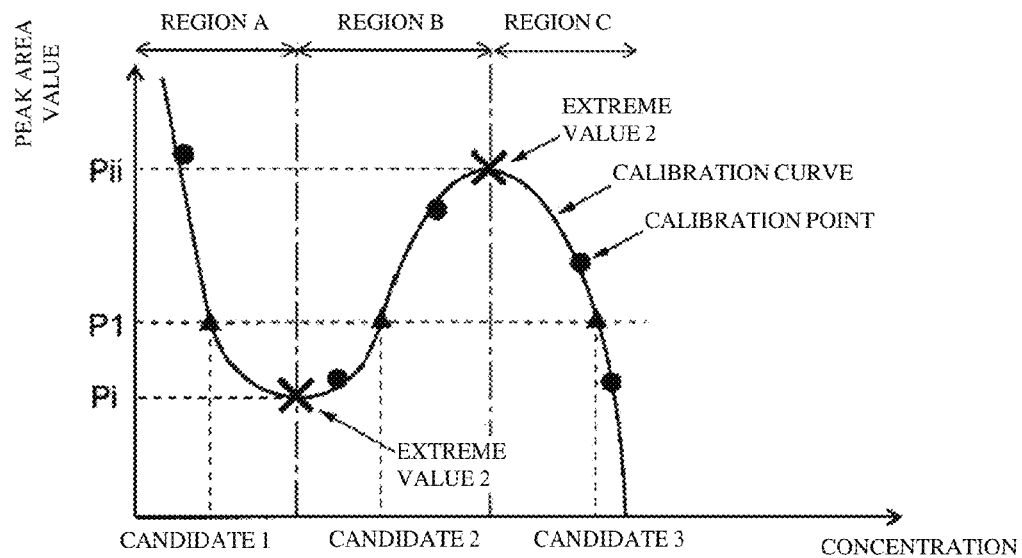
FIG. 11 is an explanatory diagram of the selection operation for a concentration value candidate when the calibration curve is a cubic function.
Figure 12:
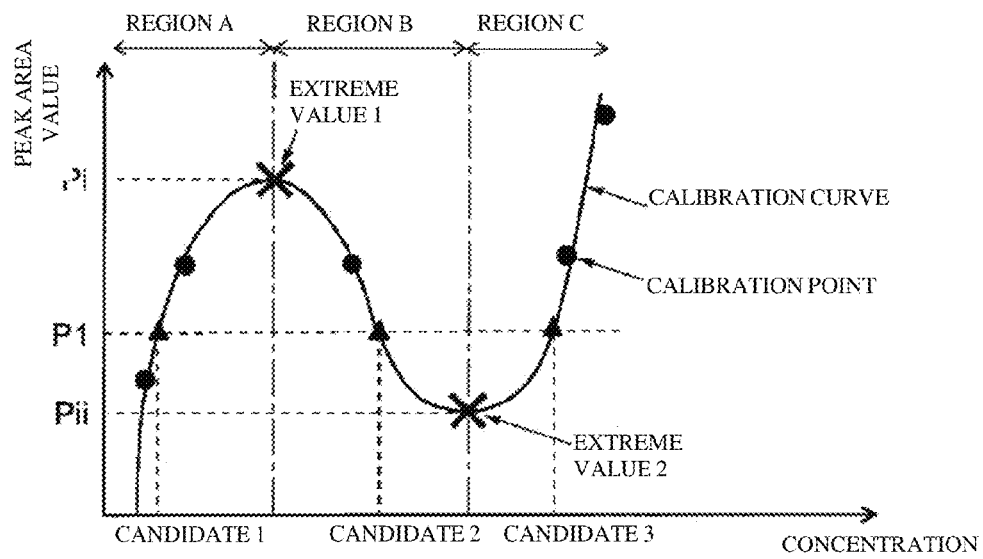
FIG. 12 is an explanatory diagram of the selection operation for a concentration value candidate when the calibration curve is a cubic function.

FIGS. 11 and 12 are explanatory diagrams of examples of the selection operation for a concentration value candidate when an assessment of "No" is made in step S18. In the example of FIG. 11, N1=1, N2=2, and N3=2. Since N2=N3>N1, an assessment of "Yes" is made in step S24, and since Pii>Pi, an assessment of "No" is made in step S25.

Therefore, as a result of the processing of step S20, a concentration value candidate 3 in region B is selected as a quantitation result for the peak area value P1. In the example of FIG. 12, N1=2, N2=1, and N3=2, and since N1=N3>N2, an assessment of "No" is made in steps S22 and S24. Therefore, as a result of the processing of step S19, a concentration value candidate 1 in region A is selected as a quantitation result for the peak area value P1.

As described above, regardless of the relationship between the calculated values N1, N2, and N3, it is possible to select a valid concentration candidate corresponding to the peak area value obtained in an actual measurement of an unknown sample as a quantitation result.

Figure 9:
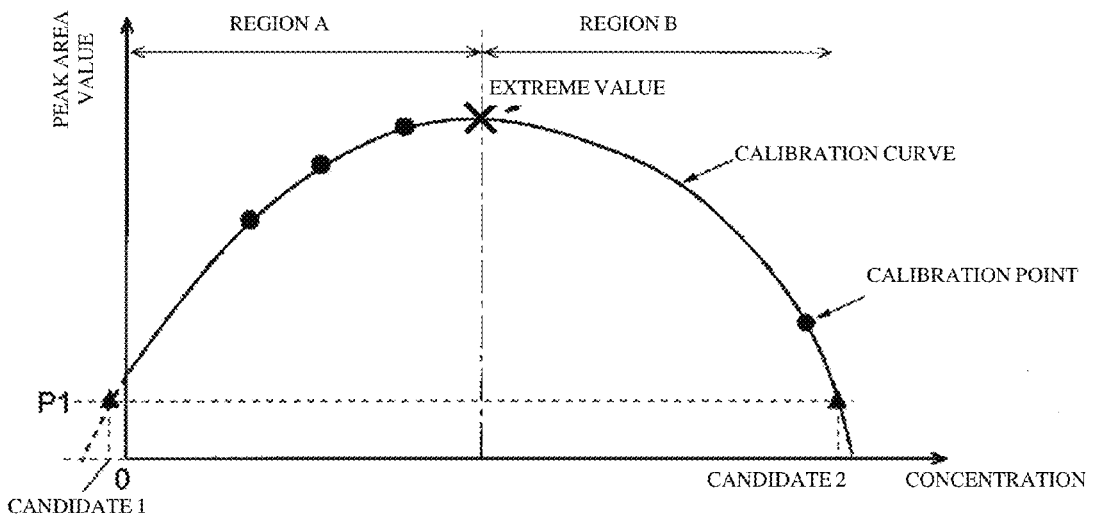
FIG. 9 is an explanatory diagram of the selection operation for a concentration value candidate when the calibration curve is a quadratic function.

Since the calibration curve is created on the basis of provided calibration points, part of the calibration curve may be drawn into a range in which the concentration value is a negative value, regardless of whether the calibration curve is a quadratic function or a cubic function. FIG. 9 illustrates an example of such a calibration curve. At this time, assuming that the peak area value obtained for an unknown sample is P1, the concentration value candidate 2 is a positive value, but the concentration value candidate 2 is a negative value. In this case, even if the concentration value candidate 1 were selected as a quantitation result by the data processing described above, it is obvious that the result would not be correct. Therefore, when the concentration value candidate selected as a quantitation result is a negative value, the value of the concentration value candidate may be displayed directly as a result, or the value may be replaced with a value of zero and displayed in different display color than a true value of zero so that it can be distinguished from a true value of zero.

Figure 13:
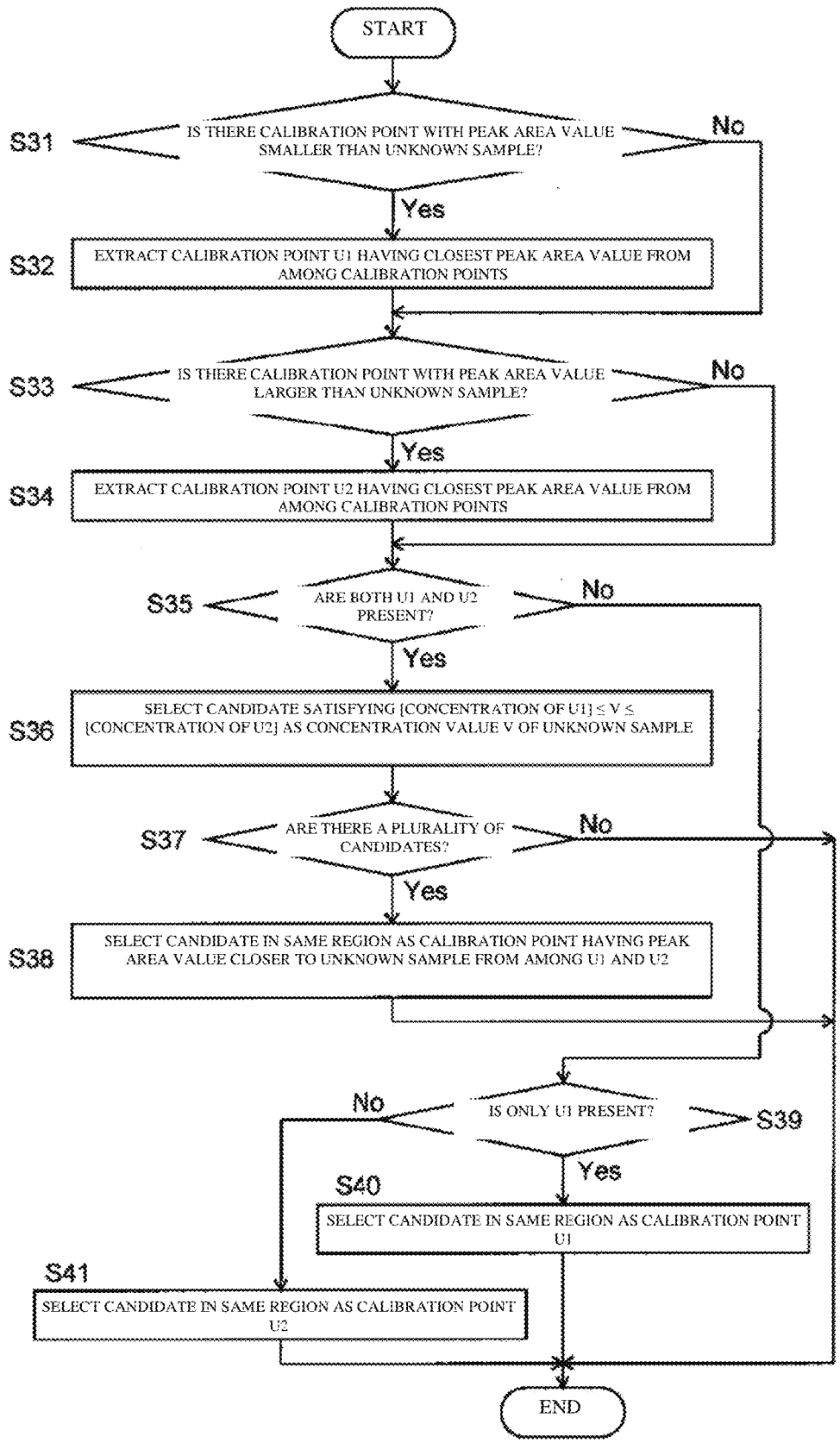
FIG. 13 is a flowchart of the processing for selecting a concentration value candidate in a second embodiment of a chromatography device provided with the data processing device for quantitation according to the present invention.

Next, another embodiment of the data processing device for quantitation according to the present invention will be described with reference to the attached drawings. The overall configuration of a chromatography device provided with the data processing device for quantitation according to this second embodiment is the same as that of the chromatography device according to the first embodiment, so an explanation thereof will be omitted here. In the data processing device for quantitation according to this second embodiment, the calibration curve is referenced with respect to a peak area value obtained for an unknown sample, and the data processing when there are two or more concentration value candidates differs from that of the first embodiment. This data processing will be described with reference to FIGS. 13 and 14. FIG. 13 is a flowchart of the data processing for selecting a concentration value, and FIG. 14 is an explanatory diagram of an example of the data processing.

When processing is initiated, the quantitative processing part 26 assesses whether there is at least one calibration point for which the peak area value is smaller than the peak area value for the unknown sample (P1 in FIG. 14) (step S31). If an assessment of "Yes" is made in step S31, a lower calibration point U1 for which the peak area value is closest to the peak area value for the unknown sample is extracted from among the calibration points (step S32). Of course, if there is only one calibration point confirmed to be present in step S31, the one calibration point is used as the lower calibration point U1. If an assessment of "No" is made in step S31, the processing of step S32 is skipped.

Next, it is assessed whether there is at least one calibration point for which the peak area value is larger than the peak area value for the unknown sample (step S33). If an assessment of "Yes" is made in step S33, an upper calibration point U2 for which the peak area value is closest to the peak area value for the unknown sample is extracted from among the calibration points (step S34). Of course, if there is only one calibration point confirmed to be present in step S33, the one calibration point is used as the lower calibration point U2. If an assessment of "No" is made in step S333, the processing of step S34 is skipped.

Figure 14:
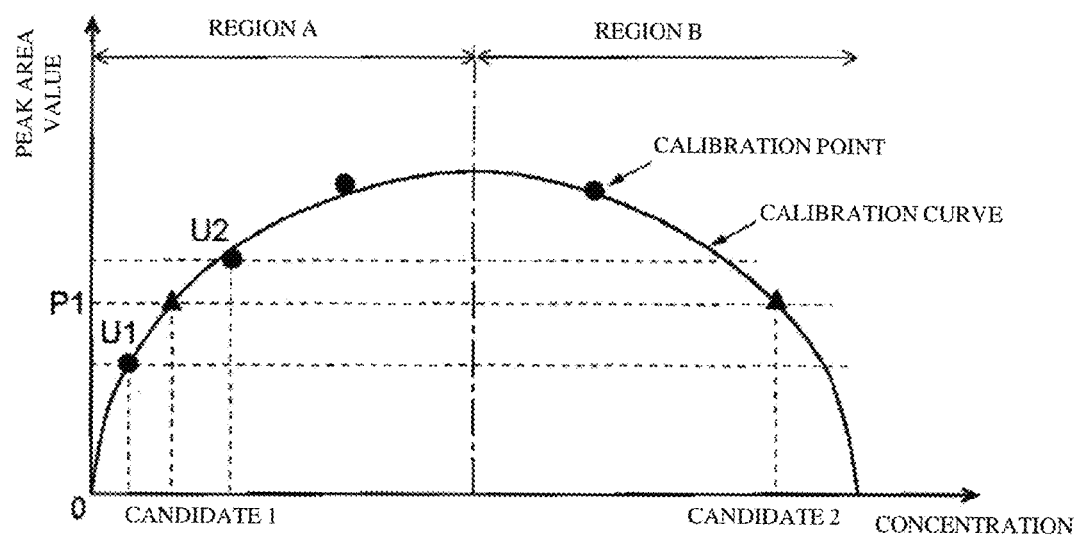
FIG. 14 is an explanatory diagram of the selection operation for a concentration value candidate when the calibration curve is a quadratic function.

FIG. 14 is an example of a case in which an assessment of "Yes" is made in both steps S31 and S33. In this case, the lower calibration point U1 and the upper calibration point U2 are set so as to sandwich the peak area value for the unknown sample.

Next, it is assessed whether both the upper calibration point U1 and the lower calibration point U2 are present (step S35). If an assessment of "Yes" is made in step S35, as illustrated in FIG. 14, the lower calibration point U1 and the upper calibration point U2 are present so as to sandwich the peak area value for the unknown sample. Therefore, a candidate for a concentration value V in which the candidate value is greater than or equal to the concentration value of the lower calibration point U1 and less than or equal to the concentration value of the upper calibration point U2 is selected as a quantitation result for the peak area value for the unknown sample (step S36). If there is only one candidate for a concentration value selected at this time ("Yes" in step S37), processing s ended directly.

On the other hand, if there are a plurality of candidates for concentration values selected in step S36 ("No" in step S37), a concentration value candidate present in the region where the calibration point in which the peak area value is closest to the peak area value for the unknown sample is present (the region described here is either region A or B in the first embodiment or one of regions A to C) is selected as a quantitation result from the two calibration points U1 and U2 (step S38). In the case of the example illustrated in FIG. 14, the two calibration points U1 and U2 are both in region A, so the concentration value candidate 1 in region A is selected as a quantitation result.

When an assessment of "No" is made in step S35, either the lower calibration point U1 or the upper calibration point U2 is not present (a case in which both are not present is not possible). Therefore, it is assessed whether only the upper calibration point U1 is present (step S39), and if an assessment of "Yes" is made in step S39, a concentration value candidate present in the same region as the lower calibration point U1 is selected as a quantitation result (step S40). If an assessment of "No" is made in step S39, only the upper calibration point U2 is present, so a concentration value candidate present in the same region as the upper calibration point U2 is selected as a quantitation result (step S41).

As described above, regardless of whether the calibration curve is a quadratic function or a cubic function, it is possible to determine a valid concentration value corresponding to the peak area value obtained in an actual measurement of an unknown sample as a quantitation result. In this case as well, it is possible to obtain a valid concentration value, irrespective of the measurement concentration range determined by the calibration point yielding the minimum concentration and the calibration point yielding the maximum concentration from among the plurality of calibration points, as in the first embodiment.

In the embodiments described above, a calibration curve indicating the relationship between peak area values and concentration values in a chromatogram was used, but it is clear that peak height values may be used instead of peak area values.

In addition, the embodiments described above were applied to chromatography devices, but the present invention can be used in any analysis device or measurement device for performing quantitative analysis on the component concentration, content, or the like in a sample using a calibration curve.

Further, the embodiments described above are merely examples of the present invention, and modifications, adjustments, and additions may be made as needed within the scope of the gist of the present invention.

EXPLANATION OF SYMBOLS

1 . . . chromatograph analysis part
2 . . . data processing part
21 . . . data collection part
22 . . . chromatogram creation part
23 . . . peak area calculation part
24 . . . calibration curve creation processing part
25 . . . calibration curve storage part
26 . . . quantitative processing part
3 . . . input part
31 . . . calibration curve degree selection part
4 . . . display part

What is claimed is:

1. A data processing device for quantitation for deriving a quantitative value corresponding to a measurement value using a calibration curve indicating a relationship between measurement values and quantitative values determined by a polynomial function, the calibration curve being created on the basis of a plurality of calibration points; the data processing device for quantitation comprising:
   an analyzer that performs a measurement on a reference sample, wherein the calibration curve is created based on a result of the measurement on the reference sample, and that performs a measurement on an unknown sample to obtain a measurement value; and
   a data processing unit, including
     a) an extreme value calculation part for finding an extreme value of the calibration curve;
     b) a quantitative value region extraction part for extracting a region where a number of calibration points is maximized by partitioning quantitative values into a plurality of regions using a quantitative value corresponding to the obtained extreme value as a boundary and determining a number of calibration points contained in each region; and
     c) a quantitative value determination part for referencing the calibration curve and, if there are a plurality of quantitative values corresponding to the measurement value, selecting a quantitative value contained in the region extracted by the quantitative value region extraction part as a valid quantitation result.

2. The data processing device for quantitation according to claim 1, wherein when a quantitative value assessed to be valid is a negative value, the quantitative value determination part uses the negative value directly as a quantitation result or replaces the quantitation result with zero and then implements a display making it possible to identify that the quantitation result was replaced.

3. The data processing device for quantitation according to claim 2, wherein the analyzer is a chromatography device, wherein the measurement value is an area value or a height value of a peak in a chromatogram, and the quantitative value is a concentration value of a sample component.

4. A data processing device for quantitation for deriving a quantitative value corresponding to a target measurement value using a calibration curve indicating a relationship between a measurement value and a quantitative value determined by a polynomial function, the calibration curve being created on the basis of a plurality of calibration points; the data processing device for quantitation comprising:

an analyzer that performs a measurement on a reference sample, wherein the calibration curve is created based on a result of the measurement on the reference sample, and that performs a measurement on an unknown sample to obtain measurement values; and a data processing unit, including a) a lower detection point extraction point for, when there are detection points for which measurement values are smaller than the target measurement value, extracting a detection point for which a measurement value is closest to the target measurement value as a lower detection point from among the detection points;

b) an upper detection point extraction point for, when there are detection points for which measurement values are smaller than the target measurement value, extracting a detection point for which a measurement value is closest to the target measurement value as an upper detection point from among the detection points; and c) a quantitative value determination part for referencing the calibration curve and, if there are a plurality of quantitative values corresponding to the target measurement value and both a lower detection point and an upper detection point are present, assessing that a quantitative value candidate contained in a quantitative value range between a quantitative value corresponding to the lower detection point and a quantitative value corresponding to the upper detection point is a valid solution.

5. The data processing device for quantitation according to claim 4, wherein when there are a plurality of quantitative value candidates contained in the quantitative value range, the quantitative value determination part finds a detection point for which a measurement point is closer to the target measurement value from among the lower detection point and the upper detection point and uses the detection point as a proximate detection point, and assesses that a quantitative value candidate contained in a region where the proximate detection point is present is the only valid solution among the plurality of regions into which the quantitative values are partitioned using quantitative values corresponding to extreme values of the calibration curve as boundaries.

6. The data processing device for quantitation according to claim 5, wherein the quantitative value determination part references the calibration curve and, if there are a plurality of quantitative values corresponding to the target measurement value and only either a lower detection point or an upper detection point is present, to assess that a quantitative value candidate contained in a region where the present lower detection point or upper detection point is present is a valid solution.

7. The data processing device for quantitation according to claim 4, wherein when a quantitative value assessed to be valid is a negative value, the quantitative value determination part uses the negative value directly as a quantitation result or replaces the quantitation result with zero and then implements a display making it possible to identify that the quantitation result was replaced.

8. A data processing method for quantitation for deriving a quantitative value corresponding to a measurement value using a calibration curve indicating a relationship between measurement values and quantitative values determined by a polynomial function, the calibration curve being created on the basis of a plurality of calibration points; the data processing method for quantitation comprising:

performing a measurement on a reference sample, wherein the calibration curve is created based on a result of the measurement on the reference sample, performing a measurement on an unknown sample to obtain a measurement value;

finding an extreme value of the calibration curve;

extracting a region where a number of calibration points is maximized by partitioning quantitative values into a plurality of regions using a quantitative value corresponding to the obtained extreme value as a boundary and determining a number of calibration points contained in each region; and referencing the calibration curve and, if there are a plurality of quantitative values corresponding to the measurement value, selecting a quantitative value contained in the region extracted by the quantitative value region extraction part as a valid quantitation result.

9. The data processing device for quantitation according to claim 8, wherein when a quantitative value assessed to be valid is a negative value, the quantitative value determination part uses the negative value directly as a quantitation result or replaces the quantitation result with zero and then implements a display making it possible to identify that the quantitation result was replaced.

10. The data processing method for quantitation according to claim 9, wherein the analyzer is a chromatography device, wherein the measurement value is an area value or a height value of a peak in a chromatogram, and the quantitative value is a concentration value of a sample component.

11. A data processing method for quantitation for deriving a quantitative value corresponding to a target measurement value using a calibration curve indicating a relationship between a measurement value and a quantitative value determined by a polynomial function, the calibration curve being created on the basis of a plurality of calibration points; the data processing method for quantitation comprising:

performing a measurement on a reference sample, wherein the calibration curve is created based on a result of the measurement on the reference sample, performing a measurement on an unknown sample to obtain measurement values;

when there are detection points for which measurement values are smaller than the target measurement value, extracting a detection point for which a measurement value is closest to the target measurement value as a lower detection point from among the detection points;

when there are detection points for which measurement values are smaller than the target measurement value, extracting a detection point for which a measurement value is closest to the target measurement value as an upper detection point from among the detection points; and referencing the calibration curve and, if there are a plurality of quantitative values corresponding to the target measurement value and both a lower detection point and an upper detection point are present, assessing that a quantitative value candidate contained in a quantitative value range between a quantitative value corresponding to the lower detection point and a quantitative value corresponding to the upper detection point is a valid solution.

12. The data processing method for quantitation according to claim 11, wherein when there are a plurality of quantitative value candidates contained in the quantitative value range, finding a detection point for which a measurement point is closer to the target measurement value from among the lower detection point and the upper detection point and uses the detection point as a proximate detection point, and assessing that a quantitative value candidate contained in a region where the proximate detection point is present is the only valid solution among the plurality of regions into which the quantitative values are partitioned using quantitative values corresponding to extreme values of the calibration curve as boundaries.

13. The data processing method for quantitation according to claim 12, wherein, when referencing the calibration curve, if there are a plurality of quantitative values corresponding to the target measurement value and only either a lower detection point or an upper detection point is present, assessing that a quantitative value candidate contained in a region where the present lower detection point or upper detection point is present is a valid solution.

14. The data processing method for quantitation according to claim 11, wherein when a quantitative value assessed to be valid is a negative value, using the negative value directly as a quantitation result or replacing the quantitation result with zero and then implementing a display making it possible to identify that the quantitation result was replaced.

* * * * *